(12) United States Patent
Smith et al.

(10) Patent No.: US 7,595,193 B2
(45) Date of Patent: *Sep. 29, 2009

(54) PROPAGATION AND/OR DERIVATION OF EMBRYONIC STEM CELLS

(75) Inventors: Austin Gerard Smith, Cambridge (GB); Thomas Grant Burdon, Edinburgh (GB)

(73) Assignee: University of Edinburgh, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/098,037

(22) Filed: Apr. 4, 2008

(65) Prior Publication Data

US 2008/0293140 A1  Nov. 27, 2008

Related U.S. Application Data

(63) Continuation of application No. 11/084,166, filed on Mar. 21, 2005, now Pat. No. 7,371,573, which is a continuation of application No. 09/786,817, filed as application No. PCT/GB99/03031 on Sep. 13, 1999, now Pat. No. 6,875,608.

(30) Foreign Application Priority Data

Sep. 11, 1998 (GB) ................................. 9819912.8

(51) Int. Cl.
*C12N 5/00* (2006.01)
*C12N 15/00* (2006.01)

(52) U.S. Cl. ...................................... 435/325; 435/455
(58) Field of Classification Search .................. 435/325
See application file for complete search history.

(56) References Cited

U.S. PATENT DOCUMENTS

| 6,146,888 A | 11/2000 | Smith et al. |
| 6,245,566 B1 | 6/2001 | Gearhart et al. |

FOREIGN PATENT DOCUMENTS

| WO | WO 94/24274 | 10/1994 |
| WO | WO 94/24301 | 10/1994 |
| WO | WO 97/30151 | 8/1997 |
| WO | WO 00/15764 | 3/2000 |

OTHER PUBLICATIONS

Niwa (Jul. 1, 1998, Genes & Development, vol. 12, p. 2048-2060.*
Alberts et al., *Mol. Biol. Cell*, Figure 15-56, (2002).
Alberts et al., *Mol. Biol. Cell*, Garland Publishing, NY, p. 722 (1994).
Atkins et al., Nature Neurosci., 1(7):602-609 (1998).
Bardwell et al., *Biochem. J.* 378:569-577 (2004) (abstract only).
Burdon et al., Cells Tissues Organs, 165(3-4):131-143 (1999).
Burdon et al., Dev. Biol., 210:30-43 (1999).
Ciruela et al., Br. J. Pharmacol., 138:751-756 (2003).
Cunnick et al., J. Biol. Chem., 273(23):14468-14475 (1998).
Daum et al., FEBS Lett., 427:271-274 (1998).
Davies et al., *Biochem. J.* 361:95-105 (2000).
Downey et al., J. Biol. Chem., 271(35):21005-21011 (1996).
Dudley et al., Proc. Natl. Acad. Sci. U.S.A., 92:7686-7689 (1995).
Duesbery et al., Science, 280:734-737 (1998).
Favata et al., J. Biol. Chem., 273(29):18623-18632 (1998).
Fourcin et al., J. Biol. Chem., 271(20):11756-11760 (1996).
Fukada et al., Immunity, 5(5):449-460 (1996).
Horiuchi et al., Biochemistry, 37:8879-8885 (1998).
Kishimoto et al., *Stem Cells*, 12 Suppl. 1:37-44 (1994), abstract only.
Lutticken et al., *Science* 263:89-92 (1994), abstract only.
MEK Inhibitors—Biocompare Buyer's Guide (available at http://www.biocompare.com/matrix/152/MEK-Inhibitors.html).
MGI webpage labeled "Search Results" listing MEK, MEK1 and MEK2 as separate proteins.
Molden et al., J. Biol. Chem., 272(31):19625-19631 (1997).
National Library of Medicine -Medical Subject Headings (available at http://www.nlm.nih.gov/cgi/mesh/2007/MB_cgi?mode=&index=19454&field=all&HM=&11=&PA=&form=&input=).
Nichols et al., Exp. Cell Res., 215:237-239 (1994).
Niwa et al., Genes Dev., 12(13):2048-2060 (1998).
Pennica et al., J. Biol. Chem., 270(18):10915-10922 (1995).
Savatier et al., Oncogene, 12(2):309-322 (1996).
Sebolt-Leopold et al., Nature Med., 5(7):810-816 (1999).
Seo et al., Free Radical Biol. Med., 40(9):1502-1512 (2006)—abstract only.
Summary of Map kinase pathway (available at http://www.brc.riken.go.jp/lab/dna/en/GENESETBANK/302mapk_ras.html).

(Continued)

*Primary Examiner*—Michael C. Wilson
(74) *Attorney, Agent, or Firm*—Finnegan, Henderson, Farabow, Garrett & Dunner, LLP

(57) ABSTRACT

Embryonic stem (ES) cells are cultured in the presence of a compound which selectively inhibits propagation or survival of cells other than ES cells. The ES cells have not been genetically altered. Instead, the compound inhibits a signalling pathway which is essential for propagation of differentiated cells but is not essential for propagation of ES cells—hence ES cells are selectively maintained in the culture.

3 Claims, No Drawings

OTHER PUBLICATIONS

SuperArray entry for U0126 (available at http://www.superarray.com/gene_function_assay_product/HTML/FA-003.html.
Taga et al., Proc. Natl. Acad. Sci. USA 89:10998-11001 (1992).
Tomaselli et al., Neurochem. Int., 46(7):513-521 (2005)—abstract only.
Tresini et al., Cancer Res., 58(1):1-4 (1998) (abstract).
Williams et al., Biochemistry, 37:9579-9585 (1998).
Yao et al., Zhongguo Zhongliu Linchuang, 32(5):290-291 (2005)—abstract only.
Yawata et al., EMBO J., 12(4):1705-1712 (1993).
Zhang et al., Bioorg. Med. Chem. Lett., 10:2825-2828 (2000).
Zhao et al., J. Antibiot., 52(12):1086-1094 (1999) (abstract).

* cited by examiner

PROPAGATION AND/OR DERIVATION OF EMBRYONIC STEM CELLS

This is a continuation of application Ser. No. 11/084,166, filed Mar. 21, 2005, now U.S. Pat. No. 7,371,573, which is a continuation of application Ser. No. 09/786,817, filed Jun. 8, 2001, now U.S. Pat. No. 6,875,608, which is a national stage application of International Application No. PCT/GB99/03031, filed Sep. 13, 1999, which claims benefit of GB 9819912.8, filed Sep. 11, 1998, all of which are incorporated herein by reference.

The present invention relates to propagation and/or derivation of embryonic stem (ES) cells and to compositions therefor.

Stem cell self-renewal underpins growth and diversification during development of the mammalian embryo and tissue repair and homeostasis in the adult. However, studies on stem cell biology have been hampered by the absence of normal, non-transformed stem cells that can be propagated in vitro. An exception to this are mouse ES cells, which can be cultured indefinitely as pluripotential stem cells when the medium is supplemented with a ligand that activates the cytokine receptor gp130. These stem cells are present only transiently in the early embryo. However, they are intrinsically tumorigenic and give rise to stem cell tumours, teratocarcinomas, when early embryos are grafted to ectopic sites. Furthermore, when the epiblast of a mouse blastocyst is explanted in culture, immortal embryonic stem (ES) cell lines can be derived.

Propagation of ES cells is dependent on the presence of the cytokine LIF, which promotes the proliferation of undifferentiated stem cells through the activation of a heteromeric complex containing two related cytokine receptors, gp130 and the low affinity LIF receptor, LIF-R.

Signal transduction via gp130 depends upon the activation of JAK kinases, a class of non-receptor tyrosine kinases that associate with the membrane proximal box1/box2 region of cytokine receptors. Upon activation, JAKs phosphorylate tyrosines in the intracellular domain of gp130 creating binding sites for proteins containing Src-homology-2 (SH2) domains. These proteins can in turn be phosphorylated, resulting in the activation of a variety of signalling molecules, including STATs (signal transducer and activator of transcription) 1 and 3, the tyrosine phosphatase SHP-2, the mitogen activated protein kinases ERK1 and ERK2, insulin receptor substrate-1 (IRS-1), Grb2 associated docking protein (Gab1) and phosphatidylinositol (PI)-3 kinase and the non-receptor tyrosine kinases hck and btk. Amongst these, both the STAT and MAPK signalling pathways have been demonstrated to play essential roles in mediating the biological responses to ligands that activate gp130 in various cell types.

STATs are a family of latent transcription factors that upon recruitment to a receptor become phosphorylated, dimerise and then translocate to the nucleus where they regulate transcription of target genes. We have recently shown that activation of STAT3 is required for maintaining the pluripotent phenotype of ES cells. Chimeric gp130 receptors unable to engage STAT3 were incapable of signalling self-renewal, whilst over-expression of a STAT3 interfering mutant caused ES cells to differentiate. However, in the absence of constitutively active forms of STAT3, we have been unable to determine whether this regulator alone is sufficient or if other signals are also required for self-renewal.

gp130 can also associate with the protein tyrosine phosphatase. This widely expressed enzyme has also been implicated in signal transduction from receptor tyrosine kinases (RTKs) and is regarded as a positive effector of the ERK signalling cascade. Although the biologically relevant substrates for SHP-2 phosphatase have not been unequivocally identified, it is significant that over-expression of catalytically inactive SHP-2 mutants can suppress receptor mediated activation of the ERK pathway. Recruitment to the gp130 receptor complex also results in tyrosine phosphorylation of SHP-2. These phosphotyrosines can serve as binding sites for the adaptor protein Grb2, which potentially couples the receptor, through interactions with SOS and Ras, to the ERK pathway. Stimulation of ERK1 and ERK2 has been demonstrated to play a role in mediating mitogenic responses of cells to growth factors, though the precise nature of this role is yet to be elucidated.

It is known to maintain cultures of ES cells in the presence of certain factors that specifically promote proliferation of ES cells, and LIF is one such factor. This does not, however, absolutely prevent differentiation; there is a continuing loss of ES cells from these cultures which accordingly in time become overgrown with differentiated cells. Thus, it remains a problem to reduce even the small rate of differentiation of ES cells when propagated in such known factors.

A further problem in this art is that the range of ES cells that can be propagated in culture is limited to just a few types, mainly mouse ES cells, despite efforts to derive ES cells from other species.

It is also known to introduce into ES cells a selectable marker that is differentially expressed in (i) ES cells and (ii) cells other than ES cells. Selection can then be used to eliminate those cells that have differentiated. But, this requires genetic alteration of the ES cells.

An object of the invention is to provide an alternative method of obtaining and/or culturing ES cells. Another object of the invention is to reduce the rate of differentiation of ES cells in known cultures. A further object is to provide culture medium components for maintenance or derivation of a culture of ES cells.

The present invention is based upon the discovery of a class of compounds that selectively promote self renewal of ES cells and/or inhibit propagation or survival of cells other than ES cells, ie selectively acting on differentiated cells.

Accordingly, the present invention provides a method of culture of embryonic stem (ES) cells, comprising maintaining the ES cells in the presence of a compound which selectively inhibits propagation or survival of cells other than ES cells.

It is an advantage that the invention uses a compound that acts on differentiated cells and enables selective removal or killing or retardation of growth of cells that have differentiated, thus facilitating retention of a relatively pure culture of ES cells. Previously, use of known ES propagating factors, say, LIF, resulted in a certain low level of differentiation of ES cells. This level can further be reduced according to the invention, using both the known factor and the compound of the invention.

The effect of the compound of the invention is selective in that its inhibitory effects are seen to a greater extent on differentiated cells than on ES cells. It is preferred that the compound has substantially no inhibitory effect on ES cells.

Preferably, the compound inhibits a signalling pathway which when activated or at least maintained, ie not inhibited, leads to or enables propagation of cells other than ES cells. In this way the compound is effectively selectively toxic to the differentiated cells compared with its effect, if any, on ES cells. Differentiated cells either die or have their growth slowed in its presence. Inhibition may be total or partial and may occur at different points along the pathway and any compound that has the effect of inhibiting the pathway is to be regarded as an inhibitor. By reference to signalling pathway it is intended to include pathways in which an endogenous or exogenous substance has a direct effect upon cell function, e.g. propagation, cell division, the cell cycle, metabolism, as well as via an indirect effect such as via receptor-mediated signalling pathways.

A further advantage of the invention is that selection of ES cells and their maintenance in culture is achieved without the need for genetic manipulation of the cells. This represents a major advantage in particular in connection with derivation of ES cells from humans. Instead, in preferred embodiments of the invention selection and/or derivation of ES cells is achieved by the discovery of a signalling pathway, which pathway can be blocked or inhibited, activation or maintenance of which is essential for propagation of differentiated cells but not for propagation of ES cells. By "essential" it is meant that the differentiated cell is at least severely handicapped, such as having its growth severely retarded or other fundamental cellular functions severely adversely affected, when the pathway is inhibited as well as meaning that cellular growth stops or the cell dies when the pathway is inhibited. If inhibition of the pathway did not actually result in death of the differentiated cell but instead a relative growth slowing such as to provide selective propagation of ES cells in culture then the effect desired in the invention is achieved. Preferably, though, differentiated cells have their growth substantially stopped compared with ES cells.

In an embodiment of the invention, the compound inhibits or reduces activity of a component of the ras/MAPK cascade. In use, the inhibitor is present in culture medium at non-toxic levels and inhibits a receptor-mediated pathway which would normally when activated lead to propagation of differentiated cells but which is not needed for propagation of ES cells. As a result, selective proliferation of ES cells is obtained.

In a particular embodiment of the invention, the compound inhibits one or more mitogen activated protein kinases, for example ERK1 and ERK2. In another embodiment of the invention, the compound inhibits SHP-2, for example by inhibiting binding of the enzyme to gp130, having a similar effect. In a further embodiment, the inhibitor inhibits MEK.

In a specific embodiment of the invention, described in examples below, the MEK inhibitor PD098059 is used to sustain ES cells in culture in an undifferentiated state. A further specific embodiment of the invention is the mitogen-activated protein kinase kinase inhibitor UO126, which is selective for MEK-1 and MEK-2 (Favata et al, 1998). Anthrax lethal factor has also been found to exhibit an MAPKK inhibitory profile similar to that of PD098059 (Duesbery et al, 1999). These various compounds may be used alone or in combination or with other factors.

The inhibitor of the invention may inhibit the cell cycle in differentiated cells, thereby preventing or slowing cell growth. A specific inhibitor of the invention inhibits MEK and induction of cyclin downstream of this enzyme is as a result disrupted; thus the various phases of the cell cycle are affected, and cyclin dependent entry into S-phase of the differentiated cells is inhibited. The selective propagation of the invention may alternatively be achieved by downregulation of a component of the ras/MAPK cascade. MKP-3 is an example of a MAP kinase phosphatase and a known downregulator of the ERKs, and in a specific example of the invention MKP-3 has been introduced into an ES cell by way of a transgene. It is further an option for selective culture of ES cells to be obtained through the use of a combination of any two or more of the inhibitors of the invention. Specifically, both a component of the ras/MAPK cascade and SHP-2 may be inhibited concurrently, though generally any combination of inhibitors is encompassed by the invention.

By "propagation", and corresponding terms, it is intended to mean that an ES cell has formed daughter cells so that the total number of ES cells is increased, ie the ES cell has survived and multiplied. "Proliferation", and its corresponding terms, is intended to have the same meaning. "Self-renewal", and its corresponding terms, is intended to mean that at least one daughter cell is identical to the parent.

According to a second aspect of the invention there is provided a method of culture of ES cells comprising maintaining ES cells in the presence of a first compound that promotes proliferation of ES cells and a second compound that enhances the response of the cells to the first compound.

This has the advantage that increased ES cell proliferation is achieved for a given amount of the first compound. In an example of the method, LIF is used to promote ES cell propagation as is known in the art and an amount of the second compound increases the effects of LIF. The first compound preferably acts through a cell-surface receptor and exerts its activity through at least one receptor subunit, and the second compound modifies an intracellular signalling pathway so as to increase the response of the ES cell to the first compound.

The second compound may suitably be an inhibitor according to the first aspect of the invention. The second compound may also bind to or otherwise affect the same receptor subunit that transduces the ES cell growth inducing signal from the first compound.

A third aspect of the invention provides a method of culture of ES cells comprising maintaining ES cells in the presence of:

(a) a compound that promotes propagation or survival of ES cells; and
(b) a compound that inhibits propagation or survival of cells other than ES cells.

Compound (a) may be selected from known compounds that promote ES cell proliferation, especially LIF, and used in combination with a compound (b) which may in turn be selected from compounds of the first aspect of the invention.

In a preferred embodiment of the invention the combination of compounds (a) and (b) is synergistic. Thus, ES cells are maintained in the presence of two factors that together increase the percentage of ES cells that self renew, and this increase is greater than the combined increase in percentage of self renewal when the two compounds are used in separate cultures.

Compound (b) suitably selectively inhibits a signalling pathway essential to propagation of cells other than ES cells, leading to selective death or growth inhibition of differentiated cells combined with propagation of remaining ES cells as mediated by compound (a). In an embodiment of the second aspect of the invention compound (b) is selected from the inhibitory compounds described above and below in relation to the first aspect of the invention, and is preferably an inhibitor of the ras/MAPK cascade. Compound (a) is typically selected from known compounds that promote proliferation of undifferentiated ES cells, such as a cytokine that activates the cytokine receptor gp130 in ES cells. LIF is one example. Another is a combination of IL-6 and sIL-6R.

The invention additionally provides in a fourth aspect a culture medium for culture of ES cells and comprising a compound that selectively inhibits propagation or survival of cells other than ES cells.

In a fifth aspect the invention provides a medium for culture of ES cells comprising a first compound that promotes proliferation or survival of ES cells and a second compound that enhances the response of the ES cells to the first compound.

In a sixth aspect the invention provides a culture medium for culture of ES cells and comprising (a) a compound that promotes proliferation or survival of ES cells, and (b) a compound that inhibits propagation or survival of cells other than ES cells.

The culture media of the invention preferably are characterised by the components as described in relation to the first to third aspects of the invention and preferably further comprise conventional culture media ingredients.

The invention still further provides a method of obtaining and/or maintaining a substantially pure culture of ES cells comprising culturing ES cells in the presence of culture medium according to any of the fourth to sixth aspect of the invention. The invention is of application without limitation to ES cell type, and may suitably be applied to vertebrate cells, in particular mammalian cells, primate cells, rodent cells, and human cells. In a specific embodiment described below in further detail, mouse cells have been used. By "ES" cells it is intended to encompass embryonic stem cells, embryonic carcinoma cells, embryonic gonadal cells, embryo-derived pluripotential stem cells and germline-derived stem cells.

A yet further aspect of the invention provides a method of deriving ES cells comprising isolating cells from an embryo or embryoid body and maintaining a culture of those cells in the presence of a compound that selectively inhibits propagation or survival of cells other than ES cells. The cells thereby obtained may then be maintained in the presence of the or a further compound that selectively inhibits propagation or survival of cells other than ES cells. In a particular embodiment described below, the method comprises developing an embryo in vivo, harvesting the embryo prior to pro-amniotic cavity formation and isolating cells therefrom, and deriving ES cells from the isolated cells or, alternatively, culturing the embryo in vivo in the presence of the compound prior to isolating ES cells therefrom.

A yet still further aspect of the invention provides a method of deriving ES cells comprising developing an embryo in vitro, isolating cells from the inner cell mass of the embryo and maintaining those cells in the presence of a compound that selectively inhibits propagation or survival of cells other than ES cells. The method may comprise removing primitive endoderm prior to culture in the presence of the compound.

In the above two aspects of the invention relating to derivation of ES cells, the compound that selectively inhibits propagation or survival of cells other than ES cells is selected from compounds which inhibit activity of the enzyme SHP-2, inhibit the ras/MAPK cascade, inhibit MEK, inhibit a mitogen activated protein kinase or inhibit cyclin dependent entry into S-phase of non-ES cells. Thus is opened the possibility to derive ES cells through the ES cell-selective mechanisms of the invention, to derive ES cells for the first time for various species from which this has hitherto not been possible.

In a specific embodiment of the present invention, ES cells were propagated in vitro whilst retaining the capacity, upon reintroduction into a blastocyst, to contribute to all cell types of the developing animal, including the germ line. These cells therefore represent a tractable experimental system with which to study the regulation of stem cell self-renewal. The identification of underlying mechanisms that regulate ES cell propagation should allow the development of improved strategies for establishing ES cell lines from other mammalian species and may contribute to our understanding of self renewal in somatic stem cells.

Ligand mediated engagement of gp130 in differentiated cells results in the recruitment and phosphorylation of the STAT3 and SHP-2 signalling molecules. Stimulation of ES cells through either endogenous gp130 or the chimeric GRgp (278) receptor increased the tyrosine phosphorylation of SHP-2. This modification was blocked when tyrosine 118 of gp130 was mutated to phenylalanine, confirming that this single tyrosine is essential for recruitment of SHP-2. In spite of this deficit, the mutated receptor was fully capable of directing self-renewal of ES cells, proving effective even at low concentrations of activating ligand. Interestingly, ES cells in which both copies of the endogenous SHP-2 gene have been mutated are viable and undergo self-renewal. Since the mutant protein carries a deletion of the N-terminal SH2 domain, a region which is known to bind to gp130 these ES cells might be expected to show an altered responsiveness to LIF—in fact, the cells exhibited impaired capacity to differentiate in vitro.

Since activation of ERK 1 and ERK2 is also associated with stimulation of gp130 in ES cells, we examined the activation of these MAP kinases by the chimeric receptors. Whereas stimulation of gp130 in ES cells triggered an increase in ERK1 and ERK2 phosphorylation, no response could be detected upon engagement of the Y118F chimeric receptor. Furthermore, treatment of ES cells with inhibitory concentrations of the MEK inhibitor PD098059 did not block but rather appeared to slightly enhance self-renewal of ES cells. Notably, however, in the absence of LIF, PD098059 did not prevent ES cell differentiation. These results establish that, in accordance with the invention, the activation of ERK1 and ERK2, via either SHP-2 or another pathway such as Shc, is not critical in maintaining the proliferation of ES cells. Selective propagation of ES cells is obtainable due to the relatively greater importance of activation of these enzymes in non-ES cells.

This lack of a requirement for gp130-dependent ERK activation may be related to the quasi-transformed nature of ES cells. An established function of ERKs in differentiated cells is to regulate the transition through G1/S, at least in part through the induction of cyclin D. However, ES have a very short G1 phase and appear to posses few of the G1 associated control mechanisms (Savatier et al., 1994; Savatier et al., 1996). Furthermore, the reduced dependence on ERK signalling is consistent with the observation that ES cells continue to proliferate in the absence of serum, a powerful mitogen and inducer of ERK activity (Johansson and Wiles, 1995). In this way, inhibition of cyclin-dependent entry into S-phase in accordance with the invention enables selective propagation and/or survival of ES cells.

In vitro differentiation of ES cells is associated with the induction of G1 cyclin expression, the establishment of a long G1 phase and a decrease in the rate of cell division (Savatier et al., 1996). This transition probably reflects the changes that normally occur in the embryo at gastrulation, after the initial rapid expansion of epiblast cells. Interestingly, inhibition of SHP-2 activity during embryonic development of either xenopus or mice is associated with failure to gastrulate normally with defects in the formation of mesodermal cell lineages. The differentiation of epiblast cells may therefore represent the point at which embryonic cells first become subservient to normal growth control mechanisms. Significantly, this is also the stage at which transplanted grafts of embryonic tissue lose the capacity to form malignant teratocarcinomas.

SHP-2/ERK activation is thus not essential for ES cell proliferation. Our results suggest that tyrosine 118 downregulates the activity of the gp130 receptor, causing a dramatic shift in dose response and prolonged activation of STAT3 in cells stimulated via the GRgp(Y118F) receptor. Until recently, SHP-2 had primarily been regarded as positive effector of signalling, either as an adaptor protein or a potential activator of src family kinases. However, a negative regulatory function was suggested both by its homology to SHP-1, a suppresser of erythropoietin receptor function, and its interaction with CTLA-4, an inhibitor of the T cell receptor. It has been reported recently that mutation of tyrosine 118 increases STAT3 signalling in neuroblastoma and hepatoma cells. Transcription from STAT3 responsive promoter constructs was also increased by overexpression of catalytically inactive SHP-2 proteins, pointing to the phosphatase as a likely mediator of this effect. This conclusion was supported by sustained phosphorylation of both the Y118F receptor and its associated JAK kinases. However, overexpression of catalytically inactive SHP-2 proteins produced only a slight shift in dose response in transfected ES cells (TB, CS unpublished), indicating that loss of phosphatase activity of SHP-2 may not be wholly responsible for the increased activity of the GRgp (Y118F) receptor.

The non-essential function of gp130-dependent SHP-2 and ERK activation in ES cells further emphasises the pre-eminent role of STAT3 in self-renewal. However, the restricted growth of GRgp(Y118F) transfectants in high concentrations of G-CSF is intriguing since it indicates that excessive signalling can interfere with ES cell growth. Hyperactivation of STAT3 is implicated in this phenotype because stimulation of the Y118F receptor results in prolonged tyrosine phosphorylation of STAT3 and sustained activation of an endogenous STAT3 target gene SOCS3. Furthermore, combined mutagenesis of some of the STAT3 docking sites can suppress the effect of the Y118F substitution.

Signals further downstream of tyrosine 118 could also influence the growth and differentiation of ES cells. The increase in self-renewal observed on treatment with the MEK inhibitor PD098059 implies that ERK activation impairs the propagation of ES cells. Interestingly, studies of gp130-dependent regulation of PC12 cell and astrocyte differentiation have suggested that activation of the MAPK pathway may antagonize signals mediated via STAT3. In both cases, reduced MAPK activity resulted in augmented transcription from STAT3 dependent reporter constructs. In ES cells treated with PD098059, self-renewal was enhanced even at saturating levels of LIF. This suggests that the effect of the inhibitors of the invention is not simply due to an inhibition of ERK activity stimulated by LIF but may occur by blocking the actions of differentiation inducers present in serum, or those secreted by ES cells and their differentiated progeny.

The present invention is described and illustrated by the following experiments:—

Exp. 1 shows gp130-dependent phosphorylation of SHP-2 in ES cells;

Exp. 2 shows effect of mutating tyrosine 118 on gp130-dependent self-renewal and growth of ES cells;

Exp. 3 shows gp130-dependent phosphorylation of ERK1 and ERK2 in ES cells;

Exp. 4 shows effect of the MEK inhibitor, PD098059, on ES cell self-renewal and ERK activation;

Exp. 5 shows effect of PD098059 on ES cell pluripotency;

Exp. 6 shows decay of activated STAT3 following stimulation of gp130 and the chimeric GRgp130 receptors;

Exp. 7 shows gp130-dependent induction of SOCS-3 gene expression in ES cells; and Exp. 8 shows the effect of an MEK inhibitor on stem cell differentiation.

Exp. 1 demonstrated gp130-dependent phosphorylation of SHP-2 in ES cells. ES cells expressing either the GRgp(278) or GRgp(Y118F) chimeric receptors were induced with IL-6 (100 ng/ml plus sIL-6R) or G-CSF (30 ng/ml) for 15 minutes. SHP-2 protein was immunoprecipitated from lysates of unstimulated or stimulated cells, fractionated on a SDS-polyacrylamide gel and transferred to a nitrocellulose membrane. The filter was probed with anti-phosphotyrosine antibody, stripped and reprobed with anti-SHP-2 antibody. The position of tyrosine phosphorylated forms of SHP-2 and two additional proteins was determined.

Exp. 2 demonstrated the effect of mutating tyrosine 118 on gp130-dependent self-renewal and growth of ES cells including stem cell renewal was mediated by GRgp(278) and GRgp(Y118F) chimeric receptors in response to G-CSF. Self-renewal, as measured by β-galactosidase expression from the Oct-4 locus was assayed after 6 days in culture with G-CSF (300 fg-30 ng/ml). Data for two independent clones are represented as means±s.e.m. for duplicate determinations of triplicate samples normalized relative to the response with IL-6 (100 ng/ml plus sIL-6R). Photomicrographs were taken of X-gal stained, representative colonies formed by GRgp (278) and GRgp(Y118F) transfectants after 6 days culture with 300 fg, 30 pg and 30 ng/ml of G-CSF. Photomicrographs were also taken of representative colonies formed by GRgp (278) and GRgp(Y118F) transfectants after 6 days culture with no cytokine, IL-6 (100 ng/ml+sIL-6R), G-CSF (30 ng/ml) or, IL-6 (100 ng/ml+sIL-6R) and G-CSF (30 ng/ml).

Exp. 3 demonstrated gp130-dependent phosphorylation of ERK1 and ERK2 in ES cells. ES cells expressing either the GRgp(278) or GRgp(Y118F) chimeric receptors were either untreated or stimulated with IL-6 (100 ng/ml plus sIL-6R) or G-CSF (30 ng/ml) for 10 or 20 minutes. Cell lysates were separated on a 10% SDS-acrylamide gel, electroblotted onto a nitrocellulose membrane and probed sequentially with antibodies specific for the active phosphorylated form of ERK and STAT3. Reprobing the stripped filter with an antibody that binds to both phosphorylated and dephosphorylated ERKs verified that equivalent amounts of protein were loaded in the samples.

Exp. 4 demonstrated the effect of the MEK inhibitor, PD098059, on ES cell self-renewal and ERK activation. To demonstrate self renewal of ES cells treated with PD098059, D027 ES cells grown at a subsaturating level of LIF (5 U/ml) were treated with PD098059 for 5 days and assayed for β-galactosidase expression from the Oct-4 locus. Data were collected as means±s.e.m for duplicate determinations of triplicate samples normalized relative to the response to LIF. To demonstrate PD098059 dependent inhibition of ERK activation, GRgp(278) transfected D027 cells were cultured with a subsaturating level of LIF (5 U/ml) and PD098059 for 48 hours. Cells were then stimulated with G-CSF (30 ng/ml) for 10 minutes, lysed in sample buffer and analyzed for ERK activation by immunoblotting with phosphospecific anti-ERK antibodies. Subsequent probing of the filter with an antibody that binds to both phosphorylated and dephosphorylated ERKs confirmed that equivalent amounts of protein were loaded in all samples. To demonstrate the effect of PD098059 on the dose response of ES cells to LIF, the dose response of D027 ES cells to LIF in 25 μM PD098059 or vehicle (0.05% DMSO) was measured by β-galactosidase expression from the Oct-4 locus. Data was collected as means±s.e.m for duplicate determinations of triplicate samples normalized relative to the maximum response of cells to treatment with LIF (111 U/ml) plus vehicle.

Exp. 5 demonstrated the effect of PD098059 on ES cell pluripotency. ZIN40 ES cells were treated with 25 μM PD098059 plus 5 U/ml LIF for 48 hours, re-fed with medium containing LIF for a further 24 hours and then microinjected into C57BL/6 blastocysts. Embryos were collected at day 9.5 of pregnancy and stained for β-galactosidase activity.

Exp. 6 demonstrated decay of activated STAT3 following stimulation of gp130 and the chimeric GRgp130 receptors. GRgp(278) and GRgp(Y118F) ES cell transfectants were stimulated with IL-6 (100 ng/ml plus sIL-6R) or G-CSF (30 ng/ml) for 25 minutes (0*), re-fed with cytokine free medium and samples were collected at 40 minute intervals. Immunoblots of cell lysates were probed sequentially with an antibody specific for the active phosphorylated form of STAT3 and then with an antibody that recognizes both phosphorylated and unphosphorylated STAT3. Activation of STAT3 was associated with the appearance of a slower migrating STAT3 species, presumed to be the serine phosphorylated form of STAT3.

Exp. 7 demonstrated gp130-dependent induction of SOCS-3 gene expression in ES cells. Northern analysis was performed on total RNA (10 g) prepared from ES cells expressing the GRgp(278), GRgp(Y126-275F) and GRgp (Y118F) receptors, unstimulated (−) or stimulated either with LIF (L, 100 units/ml) or G-CSF (G, 30 ng/ml) for the indicated times (minutes). Hybridisation of the ≈3 kb SOCS-3 mRNA and ethidium bromide staining of the 18S rRNA was observed SOCS-3mRNA was expressed and hybridization was quantitated by phosphorimage analysis and signals were normalized relative to those obtained in each cell line at 90 minutes after stimulation with LIF.

Exp. 8 demonstrated that an MEK inhibitor of the invention sustains undifferentiated ES cells in an aggregate culture.

EXAMPLE 1

Materials and Methods

Cell Culture and Transfection

ES cells were maintained without feeder cells in Glasgow modification of Eagles medium (GMEM) containing 10% fetal calf serum, 0.1 mM 2-mercaptoethanol and LIF. DO27 cells have both copies of the lif gene inactivated by homologous recombination and an IRES-βgeo reporter gene inserted within the Oct-4 gene locus. ZIN40 cells carry a nuclear localised β-galactosidase marker gene that is widely expressed in differentiated cell types. For transfections, $2 \times 10^7$ cells were electroporated with 100 µg of linearised plasmid DNA at 0.8 kV and 3 µF in a 0.4 cm cuvette using a Bio-Rad gene pulser. Stably transfected clones were selected in medium containing 20 µg/ml zeocin (Invitrogen).

Plasmid Construction

The GR/gp130 chimeric receptors were generated by fusing the extracellular domain of the human G-CSFR to an EcoRI fragment of mouse gp130 containing the transmembrane domain and the entire cytoplasmic region. The phenylalanine substitution of tyrosine 118 was introduced into the intracellular domain of gp130 by PCR overlap mutagenesis. The PCR product was substituted into the GRgp(278) chimaera and sequenced. The receptor cDNAs were inserted within expression vector pCAGIZ. This vector contains a bicistronic expression cassette, consisting of cytomegalovirus enhancer-human β-actin promoter, a site for insertion of the receptor cDNA, an internal ribosome entry site (IRES) and the zeocin resistance gene.

Self-Renewal Assay

Expression of β-galactosidase from the Oct-4 locus in DO27 cells was quantitated in an ONPG assay. Cells were plated at 5000 per well in a 24-well dishes and cultured for 6 days in the presence or absence of cytokine. When cells were treated with PD098059, they were plated at 2500 per well and cultured overnight in normal growth medium prior to addition of the inhibitor. On day 6, cells were washed once with PBS and lysed in 0.4 ml of 0.25 M Tris pH 7.5, 0.5 mM DTT, 0.5% NP40. Lysate (40 µl) was mixed with 100 µl of ONPG buffer (60 mM $Na_2HPO_4$, 40 mM $NaH_2PO_4$, 10 mM KCl, 1 mM $MgCl_2$, 50 mM 2-mercaptoethanol, 1.2 mM ONPG) in a microtitre plate, incubated at 37° C. for 2-4 hours and the absorbance was read at 420 nm. All assays were performed in triplicate.

Immunoprecipitation and Immunoblotting

One day after plating ($2-3 \times 10^6$ cells per 100 mm dish), ES cells were re-fed with medium containing 1% foetal calf serum and lacking cytokines. The following day, cells were transferred to serum free medium for 4 hours prior to stimulation with IL-6 (100 ng/ml plus soluble receptor) or G-CSF (30 ng/ml) for 15 minutes. Cells were then washed once with ice-cold PBS and scraped off in 1 ml of ice-cold lysis buffer (150 mM NaCl, 10 mM Tris.HCl pH 7.4, 0.5% NP40, 1 mM $NaVO_3$, 1 mM EDTA, 0.5 mM PMSF). Cleared lysates were incubated with 1 µg anti SHP-2 antibody (Santa Cruz) at 4° C. for 1 hour and then protein A sepharose was added and the incubation continued overnight. Immunoprecipitates were lysed in 2×SDS sample buffer, fractionated by electrophoresis on a 10% SDS polyacrylamide gel and electroblotted onto nitrocellulose. After overnight treatment with blocking buffer (25 mM Tris-HCl pH 7.4, 2.7 mM KCl, 40 mM NaCl, 0.1% Tween 20, 1% BSA) the membranes were probed sequentially with anti-phosphotyrosine antibody 4G10 (Transduction Laboratories) and anti-SHP-2 antibody. Blots were incubated with horse radish peroxidase coupled anti-rabbit IgG and developed using ECL reagents (Amersham). Antibodies were stripped from the membranes between probings by incubation at 50° C. for 30 minutes in 62.5 mM Tris.HCl pH 6.8, 2% SDS, 100 mM 2-mercaptoethanol.

For analysis of STAT3 and ERK phosphorylation, $1 \times 10^8$ ES cells were plated per well of 6-well dishes. Cells were serum starved and treated with cytokines as described above and then lysed in 100 µl SDS sample buffer. Ten microliter aliquots were fractionated on a 10% SDS polyacrylamide gel, electroblotted onto nitrocellulose and probed with anti-ERK and anti-STAT3 antibodies according to the directions provided by supplier (New England Biolabs).

Northern Blotting

RNA was prepared as described, except that the second iso-propanol precipitation was replaced by an overnight precipitation at 4° C. in 2 M LiCl to remove contaminating DNA. Total RNA (10 µg) was separated on a 0.66 M formaldehyde/agarose gel and transferred to a nylon membrane (Boehringer). Hybridisation was performed as described, using a [α-32P]dCTP labelled DNA probe. The probe was an EcoRI-NotI fragment of a SOCS3 EST plasmid (IMAGE clone number 864805, Genbank accession number AA444828 obtained from HGMP). Sequence analysis verified that the probe corresponded to nt 1666-2176 of SOCS-3 (U88328).

Chimaera Analysis

ZIN40 ES cells were injected into C57BL/6 blastocysts and transferred into pseudopregnant mice. Mice were sacrificed at day 9.5 of pregnancy and the embryos were stained with X-gal.

Results

Tyrosine 118 is Required for gp130-Dependent Phosphorylation of SHP-2 in ES Cells Previous studies in BAF pro-B cell lines have shown that gp130-dependent activation of SHP-2 and the MAPKs, ERK1 and ERK2, is mediated via tyrosine 118 (located 118 amino acid residues from the membrane) in the cytoplasmic region of gp130. To examine the functional role of tyrosine 118 in ES cells, we constructed cDNAs encoding chimaeric receptors consisting of the extracellular domain of the granulocyte colony stimulating factor receptor (G-CSFR) fused to the transmembrane and cytoplasmic region of gp130. Since ES cells do not normally express the G-CSFR and show no self-renewal response to G-CSF (data not shown), these chimaeric receptors can be used to examine signaling independently of endogenous cytokine receptors. cDNAs encoding either the unmodified chimaeric receptor, GRgp(278), or a mutated receptor in which phenylalanine had been substituted for tyrosine 118, GRgp(Y118F), were cloned into the pCAGIZ expression vector and stably introduced into DO27 ES cells by electroporation.

In several differentiated cell types, SHP-2 becomes tyrosine phosphorylated following its recruitment to a tyrosine phosphorylated gp130 receptor subunit. To examine whether SHP-2 undergoes this modification in ES cells, SHP-2 immunoprecipitates were prepared from GRgp(278) and GRgp(Y118F) transfectants following stimulation with either IL-6 (plus sIL-6R) or G-CSF and probed for phosphotyrosine by western blotting (FIG. 1A). An increase in phosphorylated SHP-2 was detected in cells stimulated through either the endogenous gp130 or the GRgp(278) receptors. Two additional tyrosine phosphoproteins co-precipitated with the phosphorylated SHP-2. The band migrating at approximately 100 kD may represent Gab1, the IRS-1-related adaptor protein previously reported to associate with phosphorylated SHP-2. No increase in phosphorylation of SHP-2 was detected following stimulation of the GRgp(Y118F) receptor, confirming that tyrosine 118 is essential for effective gp130-dependent phosphorylation of this phosphatase in ES cells.

SHP-2 Activation is Not Required for ES Cell Self-Renewal

In order to determine whether activation of SHP-2 is necessary for the propagation of ES cells, the response of GRgp130 transfectants to G-CSF was measured in a self-renewal assay. DO27 cells have a LacZ gene inserted within the stem cell specific gene, Oct-4. As a consequence, expression of this integrated reporter gene is restricted to undifferentiated ES cells and the resulting β-galactosidase activity provides a measure of stem cell self-renewal. In addition, both copies of the LIF gene have been inactivated through gene targeting, thus reducing autocrine stimulation of ES cell growth. β-galactosidase activity from two independently isolated clones for each receptor construct was measured in medium density cultures after 6 days of treatment with 300 fg-30 ng/ml G-CSF.

The data collected from Exp. 2 demonstrated that self-renewal of GRgp(278) transfectants increased in a dose dependent manner, reaching a plateau at 3-30 ng/ml G-CSF. In contrast, the maximal self-renewal response of GRgp(Y118F) ES cells was achieved at just 30 pg/ml G-CSF. The morphology of the GRgp(Y118F) colonies maintained in 30 pg/ml G-CSF was typical of undifferentiated ES cells. This result establishes that activation of SHP-2 through tyrosine 118 is not required to direct ES cell self-renewal. Equivalent levels of both receptor chimaeras were expressed at the cell surface of ES cell transfectants, as judged by binding studies with $^{125}$I-labelled G-CSF. Therefore the shift in dose response suggests that the mutant receptor may have enhanced signaling activity.

Interestingly, at higher concentrations of G-CSF, GRgp(Y118F) transfectants formed small aggregates of cells rather than the more flattened colony morphology normally associated with undifferentiated ES cells. These colonies expressed β-galactosidase and stained positive for the stem cell marker alkaline phosphatase, indicating that the ES cells remained undifferentiated. This was confirmed by the resumption of typical ES cell growth and colony morphology when, following the initial treatment with G-CSF, these cultures were refed with medium containing IL-6 plus sIL-6R.

The unusual appearance of GRgp(Y118F) cells in high concentrations of G-CSF is unlikely to be simply due to an increase in affinity of the Y118F receptor for G-CSF because this response is not observed in wild type cells treated with high levels of LIF, or in GRgp(278) transfectants treated with saturating levels of IL-6 (plus sIL-6R), G-CSF, or IL-6 (plus sIL-6R) plus G-CSF. Furthermore the phenotype of GRgp(Y118F) cells in high levels of G-CSF was maintained when cells were simultaneously stimulated with G-CSF and IL-6 (plus sIL-6R). This observation excludes the explanation that the unusual ES cell morphology is due to a partial loss of self-renewal signals and suggests that the phenotype arises from hyperactivation of signals downstream of gp130. Collectively these data point to a key role for tyrosine 118 in downregulating gp130 signaling in ES cells.

Tyrosine 118 is Necessary for Activation of ERK1 and ERK2

Since activation of SHP-2 may couple gp130 to the ERK pathway, we examined whether tyrosine 118 was also required for activation of ERK1 and ERK2 in ES cells. Activation of ERKs in GRgp130 transfectants treated with G-CSF or IL-6 (plus sIL-6R) was assessed by immunoblotting with an antibody specific for the phosphorylated (activated) forms of ERK1 and ERK2. Basal levels of activated ERK were consistently detected in untreated cells following serum starvation. Increased ERK phosphorylation was observed in cells stimulated via the endogenous gp130 and GRgp(278) receptors. This was not evident on stimulation through the GRgp(Y118F) chimaera. Reprobing with an antibody specific for the tyrosine phosphorylated form of STAT3, confirmed that both chimaeric receptors were effective at activating STAT3. These results establish that tyrosine 118 mediates activation of the ERK pathway in ES cells.

Blocking ERK Activation with PD098059 does not Impair ES Cell Propagation

The capacity of GRgp(Y118F) to signal self-renewal implies that ERK activation is not required for the propagation of ES cells. To test this hypothesis, D027 cells were cultured in the presence of the specific MEK inhibitor, PD098059. A sub-saturating concentration of LIF (5 U/ml) was used in these experiments to increase the sensitivity of the assay to changes in self-renewal signaling. Surprisingly, treatment of ES cells with 3-25 µM PD098059 did not inhibit self-renewal when compared with cells cultured in vehicle alone. More surprisingly, in fact, the level of self-renewal increased in a dose dependent manner with the maximum level being achieved at 12-25 µM. At concentrations greater than 50 µM PD098059 the growth of ES cells was impaired, possibly as a result of some non-specific inhibitory effect of the drug, resulting in small undifferentiated colonies which stained positive for β-galactosidase by X-gal staining.

To verify that ERK activation through gp130 was continuously suppressed by PD098059 in these long-term cultures, GRgp(278) cells were incubated for 48 hours with the inhibitor plus LIF and then stimulated through the chimaeric receptor with G-CSF. The immunoblot revealed that G-CSF dependent phosphorylation of ERK1 and ERK2 was progressively reduced from 3-12 µM, and effectively blocked at 25 µM PD098059. The continued proliferation of undifferentiated ES cells at inhibitory concentrations of PD098059 confirms that gp130-dependent activation of ERK1 and ERK2 is not required for the propagation of ES cells.

The effect of PD098059 on self-renewal suggested that the inhibitor might alter the dose response of ES cells to LIF. Self-renewal of ES cells was assayed following treatment with 0.1-100 U/ml LIF either in the presence of 25 µM PD098059 or vehicle (0.2% DMSO). Treatment with PD098059 increased the level of β-galactosidase activity at all concentrations of LIF. This implies that the drug does not alter the dose dependency of ES cells but rather enhances their response to LIF. Significantly, PD098059 did not block the differentiation of ES cells in the absence of LIF.

ES Cells Propagated in PD098059 Remain Pluripotent

ES cell colony morphology and Oct-4 expression are reliable indicators of the undifferentiated phenotype, but do not establish that the cells are pluripotent. We therefore determined whether ES cells propagated in the absence of gp130-dependent ERK signaling have the capacity to incorporate into the developing embryo and differentiate appropriately. Cells were cultured at low density (1000 cells/cm$^2$) for 48 hours in the presence of LIF plus 25 µM PD098059, or in the absence of LIF. They were then re-fed with medium containing LIF but lacking the inhibitor for a further 24 hours before microinjection into mouse blastocysts. ZIN40 cells were used in this experiment, since they carry a nuclear localised β-galactosidase marker that is widely expressed in differentiated cell types. Staining of mid-gestation embryos for β-galactosidase revealed that ES cells treated with PD098059 contributed to chimaeras. However, cells cultured in the absence of LIF for 48 hours were incapable of colonizing the embryo. This result confirms that gp130-dependent ERK activity is not required for maintaining the pluripotency of ES cells.

Attenuation of the STAT3 Signal is Mediated Via Tyrosine 118

We have previously established that activation of STAT3 is essential for gp130-dependent self-renewal of ES cells. To determine whether mutating tyrosine 118 affects this key regulator, activation of STAT3 was compared in GRgp(278) and (Y118F) transfectants. The acute stimulation of cells for 25 minutes with 30 fg/ml to 300 ng/ml of G-CSF did not reveal a significant difference between the levels of tyrosine phosphorylation of STAT3 induced by the chimaeric receptors. However, signaling through the receptors was distinguished when the duration of the STAT3 signal was examined. Cells were stimulated with either G-CSF or IL-6 (plus sIL-6R) for 25 minutes, re-fed with cytokine free medium and then samples were collected at 40 minute intervals. A similar time course for the decay of phosphorylated STAT3 was obtained following stimulation through either the endogenous gp130 receptor or GRgp(278), with the signal being undetectable at 120 minutes. In contrast, the activation of STAT3 was sustained in G-CSF treated GRgp(Y118F) cells and could still be detected at 160 minutes. This result indicates that tyrosine 118 mediates a signal that normally attenuates the activation of STAT3.

Substitution of Tyrosine 118 Leads to Hyperinduction of a Chromosomal Target Gene In order to investigate whether the prolonged activation of STAT3 influenced gene regulation in ES cells, we examined the expression of SOCS genes. These genes are rapidly induced by cytokines and encode proteins that can function as negative regulators of cytokine receptor function. SOCS-1 is a STAT3 target in M1 cells but this may not be the case in ES cells as we have not observed any increase in SOCS-1 expression in response to LIF. In contrast, expression of SOCS-3 was transiently induced in ES cells stimulated either through the LIFR/gp130 complex with LIF or through the GRgp(278) chimaera. The peak level of observed expression occurred at 90 minutes after addition of cytokine, and returned close to uninduced levels by 3 hours. There was no induction of SOCS-3 transcripts in ES cells stimulated through a chimaeric receptor, GRgp(Y26-275F), in which the four STAT3 docking sites have been eliminated by site directed mutagenesis. This result implies that the SOCS-3 gene is a target for STAT3 in ES cells. Significantly, following activation of the GRgp(Y118F) receptor the peak level of SOCS-3 expression obtained at 90 minutes was enhanced and in contrast to stimulation through the LIF receptor or GRgp(278), SOCS-3 mRNA levels remained elevated until at least 6 hours post-stimulation. It seems likely therefore that the prolonged activation of STAT3 results in enhanced expression of its target genes. This may underlie the shift in dose response to G-CSF observed for GRgp(Y118F) transfectants.

MEK Inhibitor PD089059 Sustains Undifferentiated ES Cells in Aggregate Culture.

Aggregation induces ES cells to differentiate and form structures known as embryoid bodies that contain multiple differentiated cell types. Undifferentiated cells are largely or wholly eliminated during embryoid formation due to induced differentiation and/or apoptosis.

IOUD2 ES cells, which carry a targeted integration of βgeo into the Oct4 locus were used to enable visualisation of undifferentiated cells by histochemical staining for β-galactosidase. Aggregates were formed in hanging drops by seeding 100 cells/20ϕl drop in the presence of 0, 25, 50, 75 or 100 µm PD089059. Aggregates were maintained for 6 days, then transferred to gelatin-coated dishes and allowed to attach overnight. Cultures were then fixed and stained for β-galactosidase activity. In the absence of the Mek inhibitor, the embryoid bodies were well differentiated and very few Oct4 β-galactosidase expressing cells were present in the outgrowths. In the presence of PD089059 however, the representation of undifferentiated β-galactosidase positive cells increased in a dose dependent fashion. At PD089059 concentrations of 75-100 µm, the great majority of cells were undifferentiated. The numbers of undifferentiated cells in these conditions vastly exceeded these present in control cultures in the absence of MEK inhibitor, therefore this result is not simply due to ablation of cells. This finding indicates that ERK activation is critical to the process of embryoid body differentiation and that differentiation of stem cells can be prevented by reducing or abolishing Mek activity.

EXAMPLE 2

Derivation of Stem Cell Lines

In order to isolate stem cell lines, embryos were developed in vivo and allowed to implant then harvested prior to pro-amniotic cavity formation (6.5 dpc equivalent). Epiblasts were microdissected and placed in suspension culture in ES cell medium in the presence of PD098059. After several days in suspension culture the epiblasts were dissociated and plated on tissue culture plastic. PD098059 was maintained in the culture medium until expanding populations of undifferentiated stem cells were generated. Stem cell lines were also derived from embryos developed in vitro by immunosurgical isolation of the ICM at the blastocyst stage followed by microsurgical removal of the primitive endoderm and culture in ES cell medium plus PD098059.

In accordance with the invention, the independence of ES cell self-renewal from ERK activation has important practical applications. Inhibitors such as of the Ras/MAPK pathway promote the propagation of undifferentiated ES cells. By suppressing the growth and maturation of differentiated cell types, such inhibitors facilitate the routine manipulation and de novo derivation of ES cells.

EXAMPLE 3

Expression of MKP-3 Transgene

A transgene coding for MKP-3 was inserted into an ES cell and a culture of ES cells obtained therefrom expressing MKP-3. It was observed that a culture highly purified in respect of ES cells was maintained and that differentiation of these ES cells was substantially reduced compared with differentiation of ES cells in a control culture not expressing the MKP-3 transgene. This experiment also provides genetic evidence in support of the invention.

REFERENCES

Dudley, D. T., L. Pang, S. J. Decker, A. J. Bridges, and A. R. Saltiel. 1995. A synthetic inhibitor of the mitogen-activated protein kinase cascade. *Proc. Natl Acad. Sci. USA.* 92:7686-7689.

Duesbery N S et al, J Appl Microbiol, August 1999, 87(2), pp 289-293. Anthrax lethal factor causes proteolytic inactivation of mitogen-activated protein kinase kinase.

Favata M F, et al, J Biol Chem, 17 Jul. 1998, 273(29), pp 18623-32. Identification of a novel inhibitor of mitogen-activated protein kinase kinase.

Johansson, B. M., and M. V. Wiles. 1995. Evidence for involvement of Activin A and Bone morphogenetic protein 4 in mammalian mesoderm and hematopoietic development. Mol. Cell. Biol. 15:141-151.

Pages, G., P. Lenormand, G. L'Allemain, J. C. Chambard, S. Meloche, and J. Pouyssegur. 1993. Mitogen-activated protein kinases p42mapk and p44mapk are required for fibroblast proliferation. Proc Natl Acad Sci USA. 90:8319-8323.

Savatier, P., S. Huang, L. Szekely, K. G. Wiman, and J. Samarut. 1994. Contrasting patterns of retinoblastoma protein expression in mouse embryonic stem cells and embryonic fibroblasts. *Oncogene.* 9:809-818.

Savatier, P., H. Lapillonne, L. A. van Grunsven, B. B. Rudkin, and J. Samarut. 1996. Withdrawal of differentiation inhibitory activity/leukemia inhibitory factor up-regulates D-type cyclins and cyclin-dependent kinase inhibitors in mouse embryonic stem cells. *Oncogene.* 12:309-322.

The invention claimed is:

1. A cell-free culture medium, comprising a compound that inhibits MEK-1, MEK-2, or both MEK-1 and MEK-2.

2. The cell-free culture medium of claim 1, wherein the compound is U0126.

3. The cell-free culture medium of claim 1, wherein the compound is PD098059.

* * * * *